US00PP12012P2

(12) United States Plant Patent
Brown

(10) Patent No.: US PP12,012 P2
(45) Date of Patent: Jul. 24, 2001

(54) PETUNIA PLANT NAMED 'COBINK'

(75) Inventor: Graham Noel Brown, Baulkham Hills (AU)

(73) Assignee: University of Sydney Plant Breeding Institute, Camden (AU)

( * ) Notice: Subject to any disclaimer, the term of this patent is extended or adjusted under 35 U.S.C. 154(b) by 0 days.

(21) Appl. No.: 09/450,096

(22) Filed: Nov. 29, 1999

(51) Int. Cl.[7] ..... A01H 5/00
(52) U.S. Cl. ..... Plt./356
(58) Field of Search ..... Plt./356

(56) References Cited

PUBLICATIONS

Upov–Rom GTITM Computer Database, 2000/06, GTI Jouve Retrieval Software, citation for 'Cobink'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Petunia plant named 'Cobink', characterized by its mounded and outwardly spreading plant habit; freely and continuous branching habit; and numerous pink double flowers.

1 Drawing Sheet

BACKGROUND OF THE INVENTION

The present invention relates to a new and distinct cultivar of Petunia plant, botanically known as *Petunia axillaris*, and hereinafter referred to by the cultivar name Cobink.

The new Petunia is a product of a planned breeding program conducted by the Inventor in Cobbitty, New South Wales, Australia. The new Petunia originated from a cross made by the Inventor in 1997 of a proprietary selection of *Petunia axillaris* identified as X96.410.1 as the female, or seed, parent with the *Petunia axillaris* cultivar Silk Road, U.S. Plant patent application Ser. No. 09/450,095, as the male, or pollen, parent. The new Petunia was selected on the basis of its flower form, flower color and spreading growth habit.

Asexual reproduction of the new cultivar by terminal cuttings taken at Cobbitty, New South Wales, Australia, has shown that the unique features of this new Petunia are stable and reproduced true to type in successive generations.

SUMMARY OF THE INVENTION

Plants of the cultivar Cobink have not been observed under all possible environmental conditions. The phenotype may vary somewhat with variations in environment such as temperature, light intensity, daylength, and fertility level without, however, any variance in genotype.

The following traits have been repeatly observed and are determined to be the unique characteristics of 'Cobink'. These characteristics in combination distinguish 'Cobink' as a new and distinct cultivar:

1. Mounded and outwardly spreading plant habit.
2. Freely and continuous branching habit.
3. Numerous double pink flowers.

Compared to plants of the single-flowered female parent, the selection X96.410.1, plants of the new cultivar have darker pink-colored flowers.

Plants of the male parent, the cultivar Silk Road, differ from plants of the new cultivar primarily in flower color as plants of 'Silk Road' have white-colored flowers.

Plants of the cultivar Cobink are similar in flower color to plants of the single-flowered cultivar Cascadia Charme, not patented. However in side-by-side comparisons conducted in Encinitas, Calif., plants of the cultivar Cobink differ from plants of the cultivar Cascadia Charme in the following characteristics:

1. Plants of the new Petunia are more compact than of plants of the cultivar Cascadia Charme.
2. Plants of the new Petunia have slightly smaller leaves and shorter internodes than plants of Cascadia Charme.
3. Plants of the new Petunia flower somewhat later than plants of the cultivar Cascadia Charme.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors.

The photograph at the top of the sheet comprises a side perspective view of three typical plants of 'Cobink' grown in a 25-cm container.

The photograph at the bottom of the sheet comprises close-up views of typical flower buds, open flowers and leaves of 'Cobink' (left side of photograph) and 'Cascadia Charme' (right side of photograph).

DETAILED BOTANICAL DESCRIPTION

The following observations, measurements and values describe plants of the new cultivar grown three plants per 25-cm containers in Encinitas, Calif. For the first six weeks after planting, plants were grown in plastic-covered greenhouses with average day and night temperatures of 23.3 and 18.9° C., respectively, and light levels averaging 3,000 foot-candles. Plants were then grown in full sun for about 12 weeks with day and night temperatures averaging 18 and 13°

C., respectively, and light levels averaging 8,000 foot-candles.

Color references are made to The Royal Horticultural Society Colour Chart except where general terms of ordinary dictionary significance are used.

Botanical classification: *Petunia axillaris* cultivar Cobink.

Parentage:

*Female parent.*—Proprietary *Petunia axillaris* selection identified as X96.410.1, not patented.

*Male parent.*—*Petunia axillaris* cultivar Silk Road, U.S. Plant patent application filed concurrently.

Propagation:

*Type cutting.*—Terminal vegetative cuttings.

*Time to initiate roots.*—About 10 days at 22° C.

*Time to produce a rooted liner.*—About 21 days at 22° C.

*Root description.*—Fine, fibrous.

Plant description:

*Form.*—Indeterminate; mounded and outwardly spreading.

*Usage.*—Appropriate for hanging baskets and various sizes of patio containers.

*Plant height* (*from soil level to top of plant plane*).—About 18 cm.

*Area of spread.*—About 37 cm.

*Vigor.*—Vigorous; moderate growth rate.

*Branching habit.*—Very freely branching with about 22 lateral branches per plant; dense and bushy plants.

*Lateral branches.*—Length: About 27 cm. Diameter: About 3.5 mm. Internode length: About 1.2 cm. Texture: Pubescent. Color: 144B.

*Foliage description.*—Leaves simple, generally symmetrical and long persisting. Leaf arrangement alternate before flowering, opposite after flowering. Quantity per lateral branch: Typically more than 50. Length: About 4.9 cm. Width: About 2.5 cm. Shape: Elliptic. Apex: Rounded. Base: Attenuate. Margin: Entire. Texture: Scattered pubescence on both surfaces, coarse; grandular, viscid. Color: Young foliage, upper surface: 146A. Young foliage, lower surface: 146B. Mature foliage, upper surface: 147A; venation, 146B. Mature foliage, lower surface: 147B, venation, 146C. Petiole: Length: About 1 cm. Diameter: About 4 mm. Color: 146C.

Flower description:

*Flower type and habit.*—Double pink flowers; flowers face upward and outward; single, axillary. Flowers persistent. Flowering continuous.

*Natural flowering season.*—Long day responsive; flowering from spring through fall.

*Quantity.*—Freely flowering with about 80 flowers per plant.

*Fragrance.*—Not detected.

*Flower longevity on the plant.*—About 4 to 7 days.

*Flower buds* (*showing color*).—Length: About 2.7 cm. Diameter: About 1.3 cm. Shape: Obovoid. Color: 68C.

*Corolla.*—Arrangement/appearance: Outer whorl of about five petals, fused into a flared trumpet, ruffled; typically more than 10 inner petaloids, separate and gathered at base, curled towards apex, petaloids irregular in shape and size. Flower diameter: About 6 cm. Flower tube length: About 2.5 cm. Flower throat diameter, distal end: About 1.5 cm. Flower tube diameter, proximal end: About 5 mm. Petal length from throat: About 2.5 cm. Petal width: About 2.8 cm. Petal shape: Ruffled fan-shaped. Petal apex: Rounded. Petal margin: Entire. Texture: Smooth, velvety; somewhat viscid. Color: Petal, upper surface, when opening: 73A to 73B. Petal, lower surface, when opening: 68D. Petal, upper surface, opened flower: 68A at apex, becoming lighter, 68B and 68C, towards base; venation, 145A and 184A. Color fading to 68C with subsequent development. Petal, lower surface, opened flower: 68B to 68C; venation, 145A. Flower throat (inside): 150D to 150C towards base; venation, 145A and 184A. Flower tube (outside): 150D; venation, 145A and 184A.

*Sepals.*—Quantity: Five. Shape: Narrow, strap-like. Apex: Rounded. Margin: Entire. Aspect: Upright. Texture: Smooth. Color: Upper surface: 147A. Lower surface: 147B.

*Peduncle.*—Strength: Strong. Angle: About 45° to stem. Length: About 3.5 cm. Color: 145A.

*Reproductive organs.*—Stamens: Stamen number: About 15, some fused to petaloids. Anther shape: Ovoid. Anther length: About 2 mm. Anther color: 157C. Pollen amount: Scarce. Pollen color: 157D. Pistils: Pistil length: About 1 cm. Stigma shape: Flattened. Stigma color: 145A. Style length: About 3 mm. Style color: 145A. Ovary color: 145A.

*Seed.*—Seed production has not been observed.

Disease resistance: Resistance to pathogens common to Petunia has not been observed.

It is claimed:

1. A new and distinct cultivar of Petunia plant named 'Cobink', as illustrated and described.

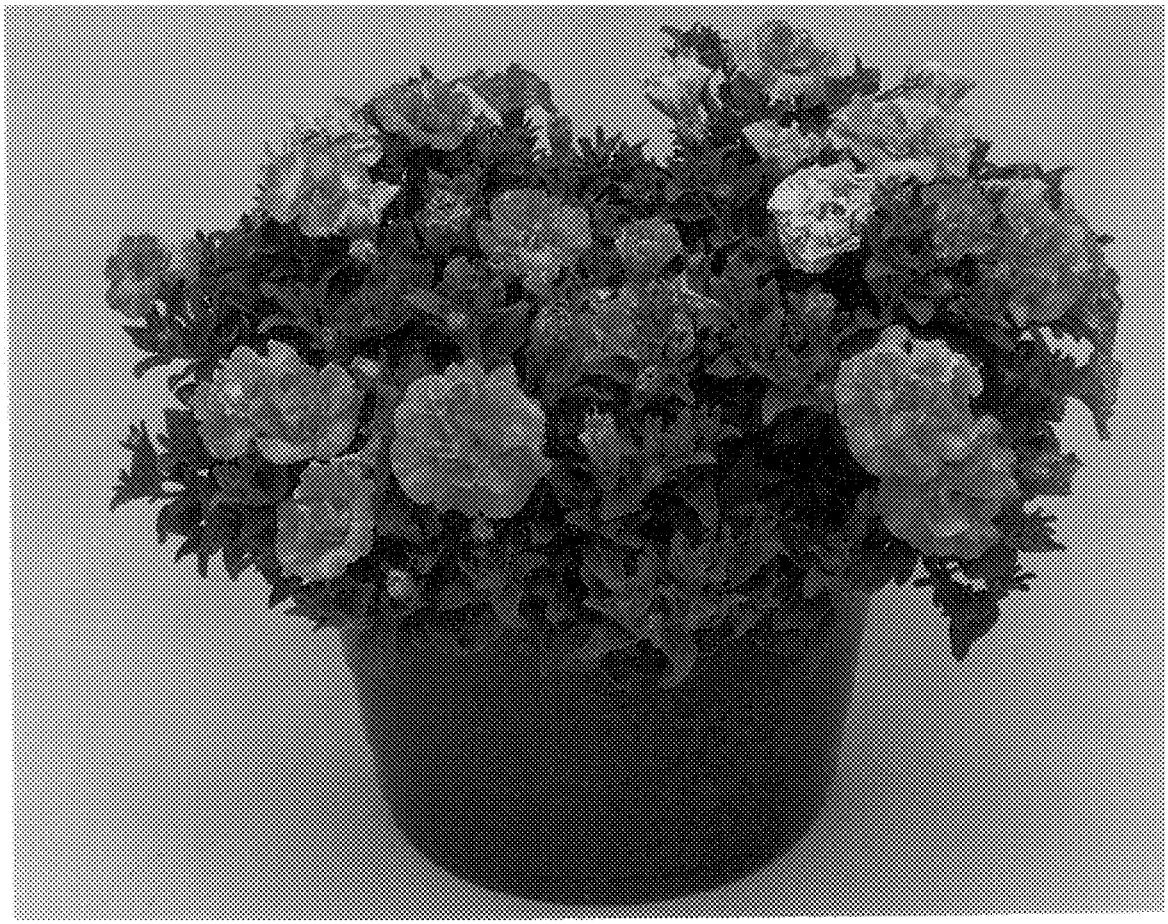
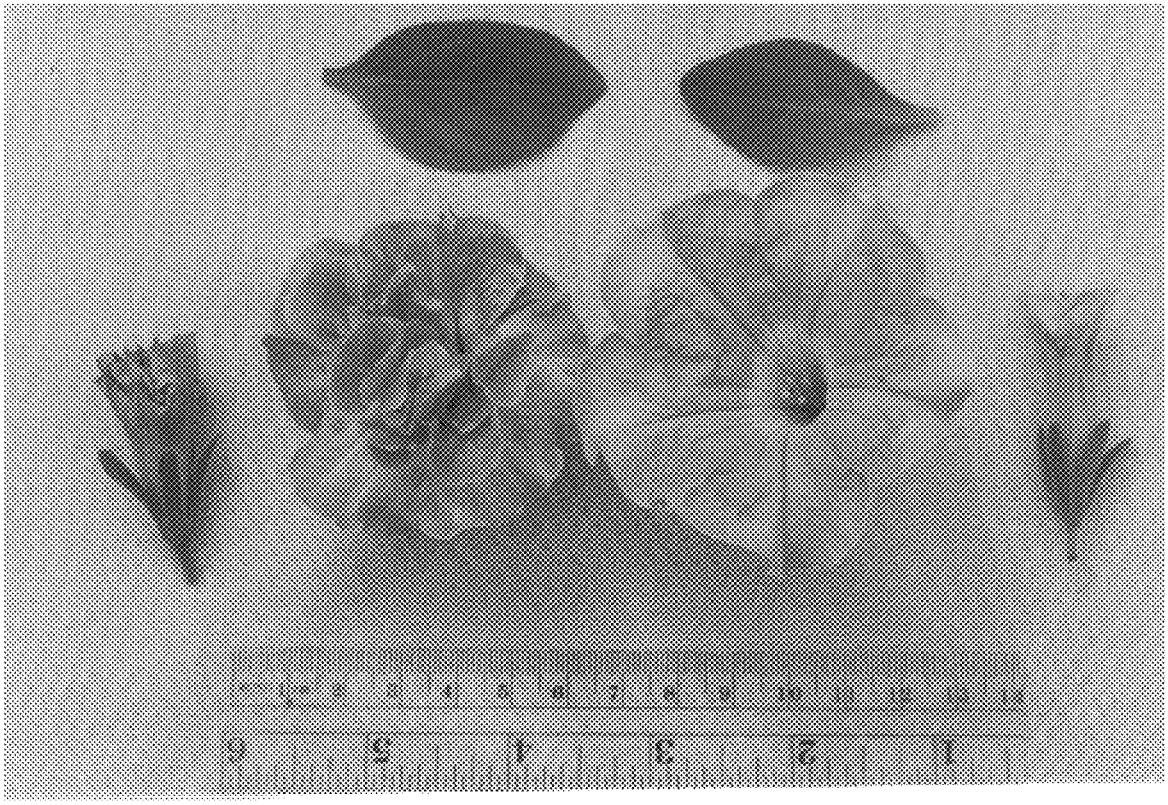

* * * * *